United States Patent [19]

Allen et al.

[11] Patent Number: 5,741,748
[45] Date of Patent: Apr. 21, 1998

[54] CATALYST PRODUCTION FOR USE IN A PROCESS FOR FLUORINATION OF HYDROCARBONS

[75] Inventors: John Graham Allen, Warrington; Daniel Howard Legg, Wirral, both of United Kingdom

[73] Assignee: Imperial Chemical Industries PLC, Great Britain

[21] Appl. No.: 403,801

[22] PCT Filed: Sep. 7, 1993

[86] PCT No.: PCT/GB93/01889

§ 371 Date: Mar. 17, 1995

§ 102(e) Date: Mar. 17, 1995

[87] PCT Pub. No.: WO94/06558

PCT Pub. Date: Mar. 31, 1994

[30] Foreign Application Priority Data

Sep. 17, 1992 [GB] United Kingdom ............. 9219720

[51] Int. Cl.⁶ .................. B01J 20/34; B01J 23/00
[52] U.S. Cl. ........................ 502/25; 502/27; 502/22; 502/319; 502/307
[58] Field of Search ................ 502/25, 27, 22, 502/319, 307

[56] References Cited

U.S. PATENT DOCUMENTS 3,755,477  8/1973  Firth et al. ............... 260/653.4
4,578,369  3/1986  Muller et al. .............. 502/36

FOREIGN PATENT DOCUMENTS

A1 0353467   2/1990   European Pat. Off. .
B 1618294   12/1974   Germany .
A1 2702360   8/1978   Germany .
290820A    12/1989   Germany ............... 502/27
2296490A    6/1986   Japan ................ 502/25

OTHER PUBLICATIONS

Encyclopedia of Chemical Technology; Four edition; vol. 6; pp. 267–269, 1979.
Encyclopedia of Chemical Technology; Third edition; vol. 6; pp. 87–88, 1993.
Ullmann's Encyclopedia of Industrial Chemistry, 1986.
Ullman's Encyclopedia of Industrial Chemistry, fifth edition
Encyclopedia of Chemical Technology, Fourth edition, Kirh–Othmer.

Primary Examiner—Glenn Caldarola
Assistant Examiner—Thuan D. Dang

[57] ABSTRACT

A process for the removal of fluoride from a spent chromium-based fluroination catalyst by contacting the catalyst with potassium hydroxide to produce a suspension of solid hydrated chromium oxide in aqueous potassium fluoride. The solid hydrated chromium oxide may be separated from the solution, washed with water and/or aqueous acid, and contacted with nitric acid to produce a chromium (III) nitrate solution from which a chromium-based catalyst may be prepared by precipitation of hydrated chromium oxide therefrom with aqueous alkali, and washing, drying and calcining the hydrated chromium oxide.

18 Claims, No Drawings

CATALYST PRODUCTION FOR USE IN A PROCESS FOR FLUORINATION OF HYDROCARBONS

FIELD OF THE INVENTION

This invention relates to a process for the removal of fluoride (F⁻) from spent chromium-based fluorination catalysts, and to a process for the recovery of hydrated chromium oxide from a spent chromium-based fluorination catalyst including the step of removing fluoride from the spent catalyst. The invention relates in a further aspect to a process for the production of chromium-based fluorination catalysts from deactivated or spent chromium-based fluorination catalysts including the step of removing fluoride from the spent catalyst, and to a process for the production of fluorinated hydrocarbons by the catalysed reaction of halogenated hydrocarbons with hydrogen fluoride in the presence of a fluorination catalyst so produced. The invention relates in particular to a process for the removal of fluoride from a spent chromia, halogenated chromia or chromium oxyfluoride fluorination catalyst, to a process for the recovery of hydrated chromium oxide from a spent chromia, halogenated chromia or chromium oxyfluoride fluorination catalyst including the step of removing fluoride, and to a process for the production of a chromia, halogenated chromia or chromium oxyfluoride fluorination catalyst from the hydrated chromium oxide so recovered.

BACKGROUND OF THE INVENTION

The production of fluorinated hydrocarbons, which may also contain halogen atoms other than fluorine, by the catalysed vapour-phase fluorination of halogenated hydrocarbons with hydrogen fluoride is well known and numerous catalysts have been proposed for use in such a process. Catalysts containing, and typically based on chromium, and in particular chromia, are frequently employed in the known processes. Thus, for example chromia, chromium oxyfluoride or a halogenated chromia may be used in the vapour-phase reaction of trichloroethylene with hydrogen fluoride to produce 1-chloro-2,2,2-trifluoroethane as described in GB Patent 1,307,224 and in the vapour-phase reaction of 1-chloro-2,2,2-trifluoroethane with hydrogen fluoride to produce 1,1,1,2-tetrafluoroethane as described in GB Patent 1,589,924. The same catalyst may be used for the fluorination of chlorodifluoroethylene to 1-chloro-2,2,2-trifluoroethane, for example in a process for the removal of chlorodifluoroethylene impurity from 1,1,1,2-tetrafluoroethane as also described in GB Patent 1,589,924.

A problem with chromium-based fluorination catalysts is that their activity decreases with time whilst they are used in hydrofluorination processes in contact with hydrogen fluoride. One reason for this deactivation is that the catalyst becomes coked due to deposition of carbon upon the surface of the catalyst. Thus it has already been proposed to reactivate or regenerate the catalyst by removing the carbon, for example by contacting the catalyst with air and hydrogen fluoride, as described for example in our co-pending published European Patent Application No. 0 475 693 or air mixed with inert gases, for example nitrogen, or mixtures thereof in order to burn off the carbon. However, such processes provide only short term reactivation for the catalysts and eventually the catalyst is deactivated to such an extent that it may no longer be usefully employed as a catalyst in such hydrofluorination processes. Such reduction in catalyst activity reaches a level at which it is no longer efficient or practical to keep on using the catalyst since the reactant conversion is reduced and attempts to increase the conversion by, for example increasing the temperature etc. lead to by-product formation and unacceptable reductions in product selectivity necessitating increased purification procedures and disposal.

In the past such deactivated or "spent" catalysts, in particular those which are based on chromium, for example chromia, halogenated chromia or chromium oxyfluoride, have been disposed of in land-fill sites.

We have now realised that these deactivated catalysts need not be wastefully disposed of, but may be recycled and we have developed a process for the recovery of chromium-based catalysts.

SUMMARY OF THE INVENTION

According to a first aspect of the present invention there is provided a process for the removal of fluoride from a spent chromium-based fluorination catalyst which comprises contacting the spent catalyst with aqueous potassium hydroxide.

We have found that contact of the spent catalyst with aqueous potassium hydroxide allows removal of fluoride ion from the spent catalyst to a substantially greater extent than the use of other alkali metal hydroxides, other bases or acids.

DETAILED DESCRIPTION

The spent catalyst which is processed by the present invention is, before deactivation due to use in hydrofluorination reactions (hereafter referred to as the "pre-spent" catalyst), a chromium based catalyst and will typically comprise chromia, halogenated chromia or chromium oxyfluoride. Such catalysts may be classified in terms of their morphology, that is by the morphology of the chromium oxide and chromium fluoride moieties within the catalyst. Thus, the chromium-based catalyst may be crystalline, amorphous or blended. Blended catalysts comprise a mixture of amorphous and crystalline chromium salts, in particular oxides and fluorides. Whilst the chromium content may be recovered from all types of morphology, amorphous, crystalline and blended by the process of the invention, the most efficient recoveries of chromium have been achieved from amorphous catalysts.

The pre-spent catalyst may also comprise other metal oxide, for example alumina or magnesia, and may also comprise activity promoting amounts of other metals, for example nickel, zinc and cobalt. For clarity, the invention will be described hereafter with reference to a chromia catalyst although the invention is not so limited.

By a "spent catalyst" there is meant a catalyst which has been employed in a hydrofluorination reaction and which has become deactivated to the extent that it may no longer be efficiently used in such processes. The extent of deactivation which may be tolerated before the catalyst must be removed will depend upon the particular fluorination reaction in which it is employed and upon the amount of by-products which the operator is prepared to tolerate. Thus, the "spent catalyst" may be recycled after any desired period of use although generally the process of the invention will be used to recycle catalysts after they have been used for such a time that the absolute conversion of the reaction which they are being used to catalyse at the particular fixed operating conditions employed has dropped by at least about 5% conversion, especially by at least about 10% conversion, although the catalyst may be referred to as spent and recycled by the process of the invention after much shorter or longer times of operation than those given above and which are given by way of guidance only.

Contact of the spent catalyst with aqueous KOH results in the production of hydrated chromium oxide which is insoluble in aqueous basic media and potassium fluoride which is very soluble in aqueous basic media. Thus, the product of the process is an aqueous solution of potassium fluoride and unreacted potassium hydroxide with hydrated chromium oxide suspended therein.

The spent catalyst may be directly contacted with the aqueous potassium hydroxide. In this case the product solution will comprise suspended solids in addition to hydrated chromium oxide, for example insoluble graphite/carbon and small amounts of insoluble crystalline chromium oxide and chromium fluoride. Alternatively the soluble components of the spent catalyst may be extracted with water and the extract may then be contacted with the aqueous potassium hydroxide. In this manner the insoluble carbon, crystalline chromium oxide and chromium fluoride residues are separated from the soluble chromium species prior to contact with the aqueous potassium hydroxide.

The concentration and amount of the aqueous potassium hydroxide which is employed will depend upon the amount and degree of fluorination of the spent catalyst.

We prefer to employ at least a stoichiometric molar excess of potassium hydroxide with respect to the fluoride content of the spent catalyst and more preferably a stoichiometric molar excess of aqueous potassium hydroxide in the range from about 1.2:1 to about 3:1, more preferably in the range from about 1.2:1 to about 1.8:1.

Generally, it is preferred to use a smaller volume of a more concentrated aqueous potassium hydroxide solution since we have found that more concentrated solutions of potassium hydroxide facilitate greater efficiency of fluoride removal, although we also prefer not to use too concentrated a solution since the volume of liquid present may be reduced to such an extent that efficient contact of the liquid and catalyst may be inhibited. The potassium hydroxide concentration is therefore preferably at least 25% w/w, more preferably at least 30% w/w so as to promote efficient removal of fluoride, but need be no more than about 75% w/w, preferably not more than 60% w/w in order that sufficient volume of liquid is present to ensure adequate contact between the catalyst and the liquid.

We have also found that the temperature at which the catalyst is contacted with the aqueous potassium hydroxide has a significant impact upon the efficiency with which, and the extent to which, fluoride is removed. Preferably, the temperature is at least 50° C. and more preferably at least 90° C. We particularly prefer to reflux the potassium hydroxide/spent catalyst mixture whilst effecting vigorous mixing.

The time for which the catalyst is in contact with the hydroxide may be varied within wide limits and is dependent upon the composition of the spent catalyst. Generally, the mixture is left in contact for at least two hours, preferably at least 5 hours. There is generally no benefit in allowing contact times of greater than 24 hours, indeed contact times longer than 24 hours may have a deleterious effect. However, the mixture may be left in contact for periods of time up to a few days, say 3 to 4 days, if desired.

The spent catalyst is typically in the form of pellets which may be directly contacted with the hydroxide. Alternatively, the particle size of the pellets may be first decreased in order to maximise the surface area of the catalyst in contact with the hydroxide. Thus, the catalyst particle size may be reduced to below about 500 microns or even less prior to contact with the hydroxide. Furthermore, in order to promote efficient contact of the catalyst with the aqueous potassium hydroxide solution, the mixture is preferably agitated.

The product of the process of the invention comprises an aqueous solution of potassium fluoride (and excess potassium hydroxide) with hydrated chromium oxide suspended therein. This product may then be further treated in order to separate the desired solid hydrated chromium oxide from the solution.

According to a second aspect of the invention there is provided a process for the recovery of hydrated chromium oxide from a spent chromium-based fluorination catalyst which comprises the steps of (a) contacting the catalyst with aqueous potassium hydroxide whereby to form a product comprising an aqueous potassium fluoride solution and solid hydrated chromium oxide and (b) separating solid hydrated chromium oxide from the aqueous solution.

Any treatment for the separation of a suspended solid from a solution may be used to effect step (b) of the process, for example, decantation, filtration, centrifugation or sedimentation. Following step (b), the hydrated chromium oxide may be contacted with further aqueous potassium hydroxide, that is step (a) may be repeated, if desired; step (b) also being repeated after each repetition of step (a).

It is also preferred that following step (b), the recovered hydrated chromium oxide is washed with water one or more times and the aqueous solution separated from the hydrated chromium oxide solid in order to remove potassium from the hydrated chromium oxide.

Furthermore, it is preferred that the recovered hydrated chromium oxide is washed at least once with an aqueous acid solution in order to reduce the residual fluoride content of the hydrated chromium oxide. We have also found that repeated water-washing which results in a gradual decrease in pH due to the steady dilution of residual KOH in the hydrated chromium oxide tends to result in the formation of linkages between the hydrated chromium oxide particles, "olation" which has a deleterious effect on the solids/liquid separation step (b). We have found that this effect may be avoided by effecting a step-change, rather than a gradual change in pH, for example by first washing with acid rather than water. Preferably therefore the solid recovered from reaction of the spent catalyst with potassium hydroxide is first washed with an aqueous acid solution before any water washings are carried out.

In a further preferred embodiment of the solids washing step of the process, the product solution from step (a) of the process may be first neutralised with aqueous acid before the solids are separated from the solution in step (b). This neutralisation may, if desired, be effected between each water wash step and each solids/solution separation.

The suspended solid hydrated chromium oxide may be washed with, for example aqueous hydrofluoric or hydrochloric acid, or a mixture thereof.

According to a preferred embodiment of this second aspect of the invention there is provided a process for the recovery of hydrated chromium oxide from a spent chromium-based fluorination catalyst which comprises the steps of (a) contacting the catalyst with aqueous potassium hydroxide whereby to form a product comprising an aqueous potassium fluoride solution and solid hydrated chromium oxide, (b) separating solid hydrated chromium oxide from the aqueous solution and (c) washing the solid recovered from step (b) with water or an aqueous acid solution and repeating step (b).

Step (c) may be repeated one or more times if desired.

The solid hydrated chromium oxide recovered after the final wash and solution/solids separation step (c) of the process may then be further treated in order to prepare a solution of a chromium (III) salt from which chromium-based fluorination catalysts are usually prepared, by precipitation of hydrated chromium oxide from that solution, followed by the conventional process steps of washing, drying, calcining and pelletising.

The solid hydrated chromium oxide recovered from step (c) of the process is preferably contacted with aqueous acid whereby to produce the chromium (III) acid salt. Chromium-based catalysts are usually manufactured from chromium (III) nitrate or chromium (III) chloride, particularly chromium (III) nitrate and preferably the hydrated chromium oxide from step (b) is contacted with an aqueous solution of nitric or hydrochloric acid, more preferably aqueous nitric acid.

According to a still further aspect of the invention there is provided a process for the recovery of chromium (III) nitrate from a spent chromium-based fluorination catalyst which comprises the steps of:

(a) contacting the spent catalyst with aqueous potassium hydroxide whereby to form a product comprising an aqueous potassium fluoride solution and solid hydrated chromium oxide, (b) separating the hydrated chromium oxide from the aqueous solution, (c) washing the solid recovered from step (b) with water or an aqueous acid solution and repeating step (b), and (d) contacting the hydrated chromium oxide of step (c) with aqueous nitric acid whereby to form chromium (III) nitrate.

In step (d) of this further aspect of the invention, the concentration and amount of aqueous nitric acid which is employed may be varied within wide limits. The concentration of the nitric acid solution may be in the range from about 20% w/w to about 70% w/w, preferably in the range from about 40% w/w to about 60% w/w. Sufficient the nitric acid solution is preferably employed to provide a stoichiometric excess of nitric acid over hydrated chromium oxide. The molar ratio of nitric acid to hydrated chromium oxide may therefore be in the range from about 2:1 to about 5:1 or greater if desired.

Step (d) is preferably carried out by refluxing the nitric acid and hydrated chromium oxide and the temperature at which this step (d) is carried out will usually therefore be about 110° C.

According to a final aspect of the invention there is provided a process for the production of a chromium-based catalyst which comprises the steps of:

(a) contacting the spent catalyst with aqueous potassium hydroxide whereby to form a product comprising an aqueous potassium fluoride solution and solid hydrated chromium oxide, (b) separating the hydrated chromium oxide from the aqueous solution, (c) washing the solid recovered from step (b) with water or an aqueous acid solution and repeating step (b), (d) contacting the hydrated chromium oxide of step (c) with an aqueous acid whereby to form a soluble chromium (III) salt, (e) precipitating and separating hydrated chromium oxide from the product of step (d) by contact with an aqueous base, and (f) washing, drying, calcining and pelletising the hydrated chromium oxide recovered from step (e).

Steps (e) and (f) may be performed by conventional techniques to those skilled in the art and are described, for example in our UK Patent No. 1,307,224, the contents of which are incorporated herein by reference.

In this final aspect of the invention and where it is desired to produce a catalyst comprising one or more metals in addition to chromium, for example a catalyst comprising an activity-promoting amount of zinc and chromia, halogenated chromia or chromium oxyfluoride, as described in our published European Patent Application No. 0 502 605, the contents of which are incorporated herein by reference, then a soluble salt of the metal, for example a halide or nitrate, may be added to the product of step (d) prior to the precipitation step (e) in order to provide sufficent amount of the metal (in addition to any soluble salt of the metal already present in the product of step (d)) from which a catalyst having the required amount of the metal in addition to chromium may be produced.

A further feature of the invention resides in use of the catalyst produced by the process defined in the fifth aspect of the invention in fluorination processes comprising reaction of a halogenated hydrocarbon with hydrogen fluoride in the vapour-phase. The catalysts so prepared as defined may be given a pre-fluorination treatment in order to activate the catalyst. Such treatments are also well described in the art, and typically comprise contacting the catalyst with hydrogen fluoride at elevated temperatures, for example temperatures in the range from about 150° C. to about 450° C.

Alkenes (unsaturated hydrocarbons), and in particular halogenated alkenes, for example trichloroethylene or halogenated alkanes of 1°–4° C. atoms, preferably containing at least one chlorine atom, may be fluorinated and examples of specific fluorinations which may be effected are the production of 1,1,1,2-tetrafluoroethane from 1-chloro-2,2,2-trifluoroethane, the production of 1-chloro-2,2,2-trifluoroethane from trichloroethylene and the conversion of 1-chloro-2,2-difluoroethylene to 1-chloro-2,2,2-trifluoroethane. Examples of other fluorination reactions in which the catalyst is useful are the reaction of perchloroethylene with hydrogen fluoride in vapour phase to produce dichlorotrifluoroethane (123), chlorotetrafluoroethane (124) and/or pentafluoroethane (125), the reaction of perchloroethylene with chlorine and hydrogen fluoride in vapour phase to produce trichlorotrifluoroethane (113), dichlorotetrafluoroethane (114/114a) and/or chloropentafluoroethane (115), the reaction of dichloromethane with hydrogen fluoride to produce difluoromethane and the reaction of 1,1,2,2-tetrachloroethane with hydrogen fluoride to produce 1,1,2,2-tetrafluoroethane.

The fluorination conditions employed may be those known to be useable when employing a catalyst comprising chromia, halogenated chromia or chromium oxyfluoride as the catalyst, for example atmospheric or superatmospheric pressure, hydrogen fluoride and temperatures in the range of 180° C. to about 500° C. depending upon the particular fluorination reaction being carried out.

A preferred embodiment of the process of the invention resides in a process for the preparation of 1,1,1,2-tetrafluoroethane which comprises reacting 1-chloro-2,2,2-trifluoroethane with hydrogen fluoride in the vapour phase in the presence of a catalyst produced as defined according to the fifth aspect of the invention. This process may be carried out under atmospheric or superatmospheric pressure at a temperature of from about 280° C. to 500° C.

The process may be one stage of a two or three-stage process, for example it may be the second stage of a process for the production of 1,1,1,2-tetrafluoroethane from trichloroethylene, the first stage being the vapour-phase fluorination of trichloroethylene with hydrogen fluoride in the presence of a chromia, halogenated chromia or chromium oxyhalide catalyst to produce 1-chloro-2,2-difluoroethylene. The catalyst produced according to the fifth aspect of the invention may be used in the first stage as well as in the second stage of this two-stage process. Typical reaction conditions for the the first stage are atmospheric or superatmospheric pressure and a temperature in the range of about 180° C. to about 300° C.

The production of 1,1,1,2-tetrafluoroethane from 1-chloro-2,2,2-trifluoroethane results in a product stream containing the toxic impurity 1-chloro-2,2,-difluoroethylene. This impurity can be removed by reacting it with hydrogen fluoride in the vapour phase in the presence of a chromia or halogenated chromia catalyst at a temperature below about 270° C., for example 150° C. to 270° C. The catalyst produced according to the fifth aspect of the invention may be employed in this reaction, thus providing a three-stage process for the preparation of 1,1,1,2-tetrafluoroethane essentially free from 1-chloro-2,2-difluoroethylene from trichloroethylene using the catalyst produced according to the fifth aspect of the invention in each of the three reaction stages.

A particularly preferred embodiment of the above-described two-stage process for preparing 1,1,1,2-tetrafluoroethane from trichloroethylene comprises the steps of:

(A) contacting a mixture of 1-chloro-2,2,2-trifluoroethane and hydrogen fluoride with a catalyst at 280°–450° C. in a first reaction zone whereby to form a product containing 1,1,1,2-tetrafluoroethane and hydrogen chloride together with unreacted starting materials, (B) passing product of step A together with trichloroethylene to a second reaction zone containing the catalyst at 180°–400° whereby to form a product containing 1-chloro-2,2,2-trifluoroethane, 1,1,1,2-tetrafluoroethane and hydrogen chloride;

(C) treating product of step B whereby to separate a mixture containing hydrogen chloride and 1,1,1,2-tetrafluoroethane from 1-chloro-2,2,2-trifluoroethane, unreacted hydrogen fluoride and unreacted trichloroethylene; and (D) feeding 1-chloro-2,2,2-trifluoroethane mixture obtained from step C together with additional hydrogen fluoride to said first reaction zone.

At least the stoichiometric amount of hydrogen fluoride is usually employed in step A of the preferred embodiment. Typical amounts include from 1 to 10 moles, and preferably from 1 to 6 moles, of hydrogen fluoride per mole of 1-chloro-2,2,2-trifluoroethane. Accordingly, the product of this reaction step will usually contain unreacted hydrogen fluoride in addition to 1,1,1,2-tetrafluoroethane, hydrogen chloride and by-products. Preferred reaction temperatures for this stage of the process are in the range from 280° C. to 400° C. with contact times of from 1 to 100 and preferably from 5 to 30 seconds at 5 to 20 bars pressure.

From 10 to 100, preferably from 15 to 60, moles of hydrogen fluoride per mole of trichloroethylene are typically employed in Step B. Again, the reaction product of this stage will normally contain unreacted hydrogen fluoride. Contact times of 1 to 100 seconds, preferably 5 to 30 seconds may be used, typically at 180°–300° C. and 5 to 20 bars pressure.

The reaction and separation steps which make up the preferred embodiment of the method of the invention may be performed using conventional equipment and techniques. Thus, for example, recovery of 1,1,1,2- tetrafluoroethane may be effected by washing the gaseous mixture (containing tetrafluoroethane and hydrogen chloride) with water and aqueous sodium hydroxide solution and then drying and condensing the tetrafluoroethane.

It is preferred that the process according to the invention, including preferred embodiments, is operated continuously. In practice, however, catalyst deactivation, necessitating periodic catalyst regeneration or reactivation may interrupt continuous operation of the process.

The invention is illustrated but not limited by the following examples.

EXAMPLE 1.

(a) KOH Hydrolysis.

100 g of a mixed oxide amorphous catalyst comprising 3% by weight zinc on chromia with a fluoride content of 46.2% by weight and which had been used to catalyse the reaction of trichloroethylene with hydrogen fluoride for 380 hours and the reaction of 1-chloro-2,2,2-trifluoroethane with hydrogen fluoride for 423 hours was reacted with 407 g of a 45% w/w potassium hydroxide solution at reflux under nitrogen for 8 hours. The reaction product mixture was centrifuged to separate a wet cake from the bulk liquors and the wet cake was washed with 100 mls of an aqueous acid solution comprising 4.5% w/w hydrogen fluoride and 0.5% w/w hydrogen chloride. The solution was again centrifuged and the solids were washed with 100 mls of deionised water and centrifuged. This water washing/centrifugation was repeated three times. The solid was dried by direct heating at 100° C. until weight loss on heating was no longer observed and the solid was analysed. 120 g of the dried solid were recovered with the following composition by weight: Cr 38.4%, Zn 2.4%, F 5.1% and K 12.5%.

(b) $HNO_3$ Digestion.

20.7g of the wet cake before drying in step (a) containing 9.4 g of solid with the composition (% w/w), Cr 39%, F 6% and K 5% was reacted with 26.6 g of a 54% by weight nitric acid solution at reflux for 8 hours. A further 10 mls of water was added to aid transfer of the reaction mixture into a centrifuge tube.

The reaction product mixture comprising chromium nitrate was separated from the residual solids by centrifugation. The residual solids weighed 1.2 g after drying representing an 87.2% uptake into solution of the starting solids in the wet cake. The solution recovered comprised chromium (III) nitrate and zinc nitrate and had a weight of 56.1 g with the following composition (% w/w): Cr 6.0%, Zn 0.45%, K 1.27% and F 0.03%.

EXAMPLE 2. PREPARATION AND ACTIVITY TESTING OF CATALYST.

This example demonstrates the activity of a catalyst prepared from an aqueous chromium (III) nitrate and zinc nitrate solution having the composition typically obtained by the process of the invention.

The composition of a similar aqueous chromium (III) nitrate and zinc nitrate solution to that obtained in step (b) of example 1 was determined as follows (% w/w based on the weight of the solution): Cr 5.1%, Zn 0.54%, K 0.05%, Ca 0.05% and F 0.05%.

A slurry of hydrated chromium and zinc oxides was precipitated from 2 liters of this aqueous chromium (III) nitrate and zinc nitrate solution by the addition of aqueous ammonia thereto. The slurry was filtered from the solution and the resultant solid was purified by slurrying and washing with water until a solid containing less than 0.02% w/w ammonium nitrate was obtained. The resultant solid was dried, calcined under nitrogen at 280° C. annd pelletised to produce the final catalyst.

20g of the catalyst as produced above and having a particle size in the range 3.5–2.0 mm was charged to each of two ½" Inconel reactor tubes connected in series and the catalyst was dried at 250° C. for 16 hours and conditioned at a pressure of 6 bar in a stream of hydrogen fluoride at 250° C. for 4 hours, followed by further conditioning in a hydrogen fluoride/air stream (volume ratio 20:1) at 380° C. for 24 hours. 1-chloro-2,2,2-trifluoroethane and hydrogen fluoride were fed to the first reactor with a molar feed ratio of 2.2:1 and at a pressure of 12 bar (corresponding to a contact time of 20 seconds at 300° C.). Trichloroethylene was fed to the product stream from reactor 1 before entering the second reactor to give a molar feed ratio of trichloroethylene to hydrogen fluoride of 17:1 (corresponding to a contact time of 20 seconds at 300° C.) and this stream was fed to the second reactor at a pressure of 12 bar. The product gases from the second reactor were scrubbed with water and sampled and the samples were analysed by Gas Chromatography.

At a first reactor temperature of 323° C. and a second reactor temperature of 250° C., the yield of 1,1,1,2-tetrafluoroethane was 12% and the conversion of trichloroethylene was 99%.

We claim:

1. A process for the treatment of a spent chromium-based fluorination catalyst which comprises the step (a) of contacting the spent catalyst with aqueous potassium hydroxide to form a product comprising an aqueous potassium fluoride solution and solid hydrated chromium oxide.

2. A process as claimed in claim 1 in which the catalyst from which the spent catalyst results through use in a hydrofluorination reaction, comprises chromia, halogenated chromia or chromium oxyfluoride.

3. A process as claimed in claim 1 in which the spent catalyst further comprises a metal selected from zinc, nickel and cobalt.

4. A process as claimed in claim 1 in which a stoichiometric molar excess of potassium hydroxide to fluoride in the spent catalyst is employed.

5. A process as claimed in claim 4 in which the molar ratio of potassium hydroxide to fluoride is in the range from about 1.2:1 to about 3:1.

6. A process as claimed in claim 1 in which the aqueous potassium hydroxide has a concentration in the range from about 25% w/w to about 75% w/w.

7. A process as claimed in claim 1 in which the spent catalyst and aqueous potassium hydroxide are refluxed together.

8. A process as claimed in claim 1 which comprises the further step (b) of separating the solid hydrated chromium oxide from the aqueous potassium fluoride solution produced in step (a).

9. A process as claimed in claim 8 in which the product solution from step (a) is neutralised with aqueous acid prior to step (b).

10. A process as claimed in claim 9 which comprises the further step (c) of washing the hydrated chromium oxide from step (b) with water or an aqueous acid solution and repeating step (b).

11. A process as claimed in claim 10 which comprises the further step of
  (d) contacting the hydrated chromium oxide product of step (c) with aqueous nitric acid whereby to form chromium (III) nitrate.

12. A process as claimed in claim 11 in which the molar ratio of nitric acid to hydrated chromium oxide in step (d) is in the range from about 2:1 to about 5:1.

13. A process as claimed in claim 11 which comprises the further steps of
  (e) precipitating and separating hydrated chromium oxide from the product of step (d) by contact with an aqueous base and
  (f) washing, drying, calcining and pelletising the hydrated chromium oxide recovered from step (e) to produce a fluorination catalyst.

14. A process as claimed in claim 13 in which the product of step (d) further comprises a soluble salt of a metal selected from zinc, nickel and cobalt.

15. A process as claimed in claim 14 in which a soluble salt of a metal selected from zinc, nickel and cobalt is added to the product of step (d).

16. A process for the production of a fluorinated hydrocarbon comprising reacting a hydrocarbon or a halogenated hydrocarbon with hydrogen fluoride in the vapour phase in the presence of a fluorination catalyst produced by the process claimed in claim 13.

17. A fluorination catalyst produced by the process of claim 14.

18. A fluorination catalyst produced by the process of claim 15.

* * * * *